United States Patent [19]  [11] 4,112,075
Baschang et al.  [45] Sep. 5, 1978

[54] FURANOSE-O-PYRIDYLCARBOXYLIC ACID ESTERS

[75] Inventors: Gerhard Baschang, Bettingen; Alex Sele, Muttenz; Jaroslav Stanek, Birsfelden; Alberto Rossi, Oberwil, all of Switzerland

[73] Assignee: Ciba-Geigy Corporation, Ardsley, N.Y.

[21] Appl. No.: 721,738

[22] Filed: Sep. 9, 1976

[30] Foreign Application Priority Data

Sep. 12, 1975 [CH] Switzerland ............... 11893/75

[51] Int. Cl.$^2$ .................. A61K 31/70; C07H 15/04
[52] U.S. Cl. .................................... 424/180; 536/1; 536/4; 536/53; 536/115; 536/119
[58] Field of Search ............... 536/4, 1, 115, 119, 536/53; 424/180

[56] References Cited

U.S. PATENT DOCUMENTS

| 3,157,634 | 11/1964 | Druey et al. | 536/4 |
| 3,538,077 | 11/1970 | Rossi et al. | 536/4 |
| 3,950,324 | 4/1976 | Gey et al. | 536/4 |

Primary Examiner—Johnnie R. Brown
Attorney, Agent, or Firm—John J. Maitner

[57] ABSTRACT

The invention relates to furanose-O-pyridylcarboxylic acid esters, such as the ethyl-2-O-methyl-3,5,6-tri-O-nicotinoyl-D-glucofuranoside, which have anti-inflammatory activity and are fibrinolysis activators. They can be used for the treatment of rheumatic and neuralgic complaints, and especially for the topical percutaneous treatment of localized inflammatory processes.

10 Claims, No Drawings

FURANOSE-O-PYRIDYLCARBOXYLIC ACID ESTERS

The invention relates to furanose-O-pyridylcarboxylic acid esters of the formula I

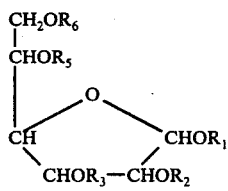

wherein at least one of the radicals $R_1$, $R_2$, $R_3$, $R_5$ and $R_6$ is pyridylcarbonyl and the remainder of the radicals $R_1$, $R_2$, $R_3$, $R_5$ and $R_6$ are lower alkyl, lower alkenyl, aryl-lower alkyl or hydrogen, or wherein $OR_1$ is hydrogen, and to processes for their manufacture.

In the foregoing text and the text which follows, lower radicals are, in particular, those with up to 7 C atoms and above all with up to 4 C atoms.

Furanose-O-pyridylcarboxylic acid esters are derived from aldohexofuranoses, such as from glucose, mannose, allose, altrose, talose, galactose, idose and gulose. These aldohexofuranoses can be in the form of D- or L-aldohexofuranoses and also in the form of mixtures of anomers or of pure α- or β-anomers.

Pyridyl in pyridylcarbonyl is 2-, 4- and especially 3-pyridyl.

Lower alkyl is, for example, isopropyl, straight-chain or branched butyl, pentyl, hexyl or heptyl, which are bonded in any desired position, and especially methyl, ethyl or n-propyl.

Lower alkenyl is, for example, 2- or 3-methallyl or 3-butenyl and especially allyl.

Aryl-lower alkyl corresponds to the abovementioned lower alkyl in the lower alkyl part and contains as aryl, in particular, optionally substituted phenyl or naphthyl, suitable substituents being, for example: halogen, such as bromine or especially chlorine, trifluoromethyl, lower alkyl, such as those mentioned above, and/or lower alkoxy, such as ethoxy, iso- or n-propoxy, iso-, tert.- or n-butoxy and especially methoxy, and it being possible for aryl to contain two or more substituents, but preferably only one substituent or no substituent. Radicals to be mentioned in particular are: 2-phenylethyl, chlorobenzyl, methylbenzyl, methoxybenzyl and benzyl.

The new compounds possess valuable pharmacological properties. Thus, they display an anti-inflammatory action, as can be shown on topical application in concentrations of 30–100 mg/ml on croton oil ear oedemas in mice, and a hyperaemising action, as can be shown on topical application, in concentrations of 30–100 mg/ml, on erythema of the skin in man. Furthermore, in rats which have a kaolin paw oedema, the compounds activate fibrinolysis on oral administration. The new compounds can therefore be used as agents for the treatment of rheumatic and neuralgic complaints and especially for the topical, percutaneous treatment of localised inflammatory processes, such as rheumatic arthropathy, rheumatism of soft tissues or superficial phlebitides. However, they are also valuable intermediate products for the manufacture of other substances, above all substances which can be used pharmaceutically.

Compounds to be singled out are compounds Ia of the formula I, wherein 1–4 of the radicals $R_1$, $R_2$, $R_3$, $R_5$ and $R_6$ are pyridylcarbonyl and the remainder of the radicals $R_1$, $R_2$, $R_3$, $R_5$ and $R_6$ are lower alkyl, lower alkenyl, phenyl-lower alkyl, halogenophenyl-lower alkyl, trifluoromethylphenyl-lower alkyl, lower alkylphenyl-lower alkyl, lower alkoxyphenyl-lower alkyl or hydrogen, or wherein $OR_1$ is hydrogen.

Compounds to be especially singled out are compounds Ib of the formula I, wherein 1–4 of the radicals $R_1$, $R_2$, $R_3$, $R_5$ and $R_6$ are pyridylcarbonyl and the remainder of the radicals $R_1$, $R_2$, $R_3$, $R_5$ and $R_6$ are lower alkyl, lower alkenyl, benzyl, halogenobenzyl, trifluoromethylbenzyl, lower alkylbenzyl, lower alkoxybenzyl or hydrogen, or $OR_1$ is hydrogen.

Compounds to be singled out above all are compounds Ic of the formula I, wherein 1–4 of the radicals $R_1$, $R_2$, $R_3$, $R_5$ and $R_6$ are pyridylcarbonyl and the remainder of the radicals $R_1$, $R_2$, $R_3$, $R_5$ and $R_6$ are lower alkyl with 1–3 C atoms, benzyl, chlorobenzyl or hydrogen, or $OR_1$ is hydrogen.

Compounds to be singled out in particular are compounds Id of the formula I, wherein 1–4 of the radicals $R_2$, $R_3$, $R_5$ and $R_6$ are pyridylcarbonyl and the remainder of the radicals $R_2$, $R_3$, $R_5$ and $R_6$ are lower alkyl with 1–3 C atoms, benzyl, chlorobenzyl or hydrogen and $R_1$ is lower alkyl with 1–3 C atoms.

Amongst all of the ranges of compounds which have been singled out, that is to say Ia, Ib, Ic and Id, the O-lower alkyl-D-glucofuranosides, especially the O-ethyl-D-glucofuranosides, are to be mentioned in particular and the compounds indicated in the examples are to be mentioned very particularly.

The furanose-O-pyridylcarboxylic acid esters can be manufactured according to methods which are in themselves known.

The procedure used for the manufacture can be that, in a compound of the formula II

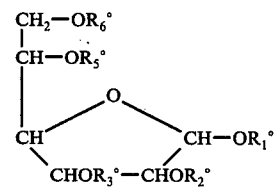

wherein at least one of the groups $OR_1°$, $OR_2°$, $OR_3°$, $OR_5°$ and $OR_6°$ represents optionally reactive esterified hydroxyl and the others have the meanings indicated for $OR_1$, $OR_2$, $OR_3$, $OR_5$ and $OR_6$ respectively, but differ from pyridylcarbonyloxy, or represent a hydroxyl group protected by a protective group, the optionally reactive esterified hydroxyl group is converted into a pyridylcarbonyloxy group and any protective groups which may be present are split off.

A free hydroxyl group in the starting material can be converted into the desired pyridylcarbonyloxy group by acylation processes which are in themselves known, for example by reacting a corresponding starting material with a pyridinecarboxylic acid or, in particular, with a reactive derivative thereof.

A reactive derivative of pyridinecarboxylic acid which is preferably used is, for example, an anhydride, including a mixed anhydride, such as the anhydride with a carbonic acid lower alkyl half-ester (which can be obtained, for example, by reacting a suitable salt, such as an ammonium salt, of the acid with a lower alkyl halogenoformate, for example ethyl chloroformate), with a hydrogen halide acid, such as hydrochloric acid, or with a suitable, optionally substituted lower alkanecarboxylic acid, for example trichloroacetic acid or pivalic acid, and also an activated ester of such an acid, for example an ester with a N-hydroxyamino compound or N-hydroxyimino compound, such as N-hydroxy-succinimide, or with a lower alkanol, especially methanol, or phenol, which contain electron-attracting groups, for example nitro groups, acyl groups, such as lower alkanoyl groups, for example acetyl groups, or aroyl groups, for example benzoyl groups, or optionally functionally modified carboxyl groups, such as carbo-lower alkoxy groups, for example carbomethoxy or carboethoxy groups, carbamoyl groups, for example N,N-dimethylcarbamoyl groups, or cyano groups, for example cyanomethanol or 4-nitrophenol.

If necessary, the reaction is carried out in the presence of a suitable condensing agent; thus, for example, an acid is reacted in the presence of a dehydrating condensing agent, such as a carbodiimide, for example dicyclohexylcarbodiimide, optionally together with a catalyst, such as a copper salt, for example copper-I chloride or copper-II chloride. An acid anhydride, especially an acid anhydride with a hydrogen halide acid, can be used, for example, in the presence of a basic, acid-binding condensing agent, such as pyridine or triethylamine, and another anhydride can be used, for example, in the presence of a suitable carbodiimide and optionally of a catalyst, such as zinc chloride.

In a starting material which contains a reactive esterified hydroxyl group, such as a halogen atom, for example a bromine or iodine atom, or a hydroxyl group esterified with an organic sulphonic acid, for example a p-toluenesulphonyloxy group, such a group can be converted into the desired pyridinecarbonyloxy group, for example by treatment with a salt of a pyridinecarboxylic acid, such as an alkali metal salt, for example a sodium or potassium salt, or a silver salt.

A protective group is, for example, an optionally substituted alkylidene radical in which the nature of the substituents is of secondary importance, such as an aralkylidene, for example benzylidene, but especially a lower alkylidene, such as isopentylidene or cycloalkylidene, such as cyclohexylidene, but above all isopropylidene.

A protective group, and especially an ylidene radical, is generally split off by treatment with water or a lower alkanol, lower alkenol or aryl-lower alkanol in the presence of an acid.

The acid used is usually a proton-acid, especially an inorganic acid, such as a mineral acid, for example a hydrogen halide acid, especially hydrochloric acid and hydrobromic acid, and also sulphuric acid or phosphoric acid, or an organic acid, such as an organic carboxylic acid, for example formic acid or oxalic acid, or an organic sulphonic acid, for example p-toluenesulphonic acid, or a mixture of acids, such as, for example, a mixture of hydrochloric acid or p-toluenesulphonic acid and acetic acid, preferably in the form of glacial acetic acid, and also a salt which has acid character.

Splitting-off is preferably effected in the presence of a diluent and it is possible for a reactant, such as an alcoholic reagent or an organic acid, such as acetic acid, at the same time also to serve as the diluent; a mixture of solvents or diluents can also be used. The reaction is preferably carried out in the presence of a hydrogen halide acid, especially hydrochloric acid, if an alcohol is used, and is preferably carried out in the presence of an organic carboxylic acid, especially formic acid or oxalic acid, and in particular in the presence of acetic acid, if water is used and the reaction is effected, if necessary, with cooling, but above all at room temperature or at elevated temperature (for example at about 25° to about 150°), optionally in a closed vessel under pressure and/or in an inert gas atmosphere, such as a nitrogen atmosphere.

If, in the above elimination reaction, an alcohol is used as the reagent in the presence of an anhydrous acid, especially hydrogen chloride, one of the two hydroxyl groups conjointly etherified by the ylidene radical, especially the hydroxyl group in the 1-position, can be etherified immediately it is liberated. The elimination reaction can, therefore, at the same time be used to introduce a hydroxyl group which is etherified as indicated into a compound which is obtainable according to the process and which, for example, does not yet contain the indicated etherified hydroxyl group.

In resulting compounds, substituents can, within the scope of the end products—and optionally independently of the manufacturing process—be introduced, split off or modified.

In a resulting compound which contains a hydroxyl group, such a group can be etherified in a manner which is in itself known to give lower alkoxy, lower alkenyloxy or aryl-lower alkoxy.

The etherification of a free hydroxyl group can be carried out, for example, by treatment with a reactive ester of a corresponding alcohol, for example with a corresponding halide, such as chloride or bromide, or a corresponding organic sulphonyloxy compound, such as a p-toluenesulphonyloxy compound, in the presence of a basic agent, such as an alkali metal hydroxide, for example sodium hydroxide or potassium hydroxide, or an alkali metal carbonate, for example sodium carbonate or potassium carbonate, or of silver oxide.

In a resulting compound which has a free 1-hydroxyl group (such a hydroxyl group can preferably be liberated when a 1,2-ylidene radical is split off), such a group can also be etherified by treating a corresponding compound with a corresponding alcohol in the presence of an acid, or with a diazo compound. Acids which can be used are mineral acids, for example hydrochloric acid, or organic carboxylic acids, for example acetic acid, or sulphonic acids, for example p-toluenesulphonic acid, and optionally mixtures of acids, such as acetic acid mixed with hydrochloric acid or p-toluenesulphonic acid, and also salts which have acid character and the reaction is preferably carried out using a mineral acid concentration of from about 0.05 N to about 1 N, above all of from about 0.1 N to about 0.5 N.

In a resulting compound which contains a hydroxyl group etherified by an optionally substituted benzyl radical, such a group can be converted into a hydroxyl group, for example by treatment with catalytically activated hydrogen, such as hydrogen in the presence of a noble metal catalyst, for example a palladium catalyst.

In a resulting compound, a lower alkenyl radical, for example an allyl radical, can be saturated by treatment with catalytically activated hydrogen, for example hydrogen in the presence of a palladium catalyst.

In a resulting compound which contains a hydroxyl group, the latter can be converted into a pyridylcarbonyloxy group, in particular in the manner described above.

In a resulting compound, a hydroxyl group etherified by a suitable 2-alkenyl radical, such as the allyl radical, can be liberated, for example by rearranging the double bond by means of treatment with a suitable base, such as an alkali metal tert.-butylate, for example potassium tert.-butylate, preferably in a suitable solvent, such as, for example, dimethylsulphoxide, and removing the resulting 1-lower alkenyl group, such as a 1-propenyl group, by oxidative hydrolysis, for example by treatment with potassium permanganate, preferably in a basic medium, such as an ethanolic alkali metal hydroxide, for example potassium hydroxide.

The new compounds can be in the form of pure α- or β-anomers or in the form of mixtures of anomers. The latter can be separated into the two pure anomers in a known manner on the basis of the physico-chemical differences between the constituents, for example by means of chromatographic separation, such as thin layer chromatography, or by any other suitable process of separation. Preferably, the more active of the two anomers is isolated.

The processes described above are carried out according to methods which are in themselves known, in the absence or, preferably, in the presence of diluents or solvents, if necessary with cooling or warming, under elevated pressure and/or in an inert gas atmosphere, such as a nitrogen atmosphere.

The invention also relates to those embodiments of the process according to which a compound obtainable as an intermediate product at any stage of the process is used as the starting material and the missing process steps are carried out, or the process is discontinued at any stage, or a starting material is formed under the reaction conditions or is used in the form of a reactive derivative. The starting materials employed are preferably those which, according to the process, lead to the compounds described above as being particularly valuable.

The starting materials are known or, if they are new, can be manufactured according to processes which are in themselves known, for example etherification of a furanose.

The pharmacologically usable compounds of the present invention can, for example, be used for the manufacture of pharmaceutical formulations which contain an effective amount of the active substance together with, or mixed with, inorganic or organic, pharmaceutically usable excipients which are suitable for topical application. Substances which can be used for the formation of the formulations are those which do not react with the new compounds, such as, for example, water, gelatine, lactose, starch, stearyl alcohol, magnesium stearate, talc, vegetable oils, benzyl alcohol, propylene glycols, white petroleum jelly or other known medicinal excipients. The pharmaceutical formulations can, for example, be in the form of creams or ointments or in a liquid form as solutions (for example as an elixir or syrup), suspensions, a jelly or emulsions. The formulations are optionally sterilised and/or contain auxiliaries, such as preservatives, stabilisers, wetting agents or emulsifiers, solubilising agents or salts for regulating the osmotic pressure, or buffers. The pharmaceutical formulations are obtained by customary methods.

The invention is described in more detail in the examples which follow. The temperatures are given in degrees centigrade.

EXAMPLE 1

51.0 g of solid nicotinoyl chloride-hydrochloride are added in portions in the course of one hour to a solution of 25.0 g of 1,2-O-isopropylidene-3-O-n-propyl-α-D-glucofuranose in 200 ml of pyridine and 100 ml of methylene chloride, at 60°–70°, with the exclusion of atmospheric moisture and whilst stirring. After the mixture has been allowed to react for a further 30 minutes, the bulk of the pyridine and methylene chloride is distilled off under a waterpump vacuum. A saturated solution of sodium bicarbonate is added to the resulting residue and the mixture is extracted with ether. The combined ether phases are washed with a little ice-cold 2 N hydrochloric acid solution, with a little of a saturated solution of sodium bicarbonate and with water. After the ether solution has been dried over sodium sulphate, it is filtered and pure 1,2-O-isopropylidene-3-O-n-propyl-5,6-di-O-nicotinoyl-α-D-glucofuranose, which after drying has a melting point of 75°–76° and an optical rotation $[\alpha]_D^{20} = -23° \pm 1°$ (c = 1.130 in chloroform), crystallises out of the filtrate on the addition of petroleum ether at 40°–70°.

30.0 g of 1,2-O-isopropylidene-3-O-n-propyl-5,6-di-O-nicotinoyl-α-D-glucofuranose are dissolved in 300 ml of a 1 N solution of hydrogen chloride gas in absolute ethanol and the solution is left to stand for 16 hours at about 25°. The reaction solution is now freed from the bulk of the ethanolic hydrochloric acid under a waterpump vacuum and the residue is dissolved in ether. The ether solution is washed with a saturated solution of sodium bicarbonate and with water, dried over magnesium sulphate, filtered and evaporated. The residue thus obtained is purified by column chromatography over 900 g of silica gel (0.02–0.6 mm) using ethyl acetate as the mobile phase. The yellowish clear oil which is thus obtained is pure ethyl-3-O-n-propyl-5,6-di-O-nicotinoyl-D-glucofuranoside; Rf value 0.37 (β-anomer) and 0.51 (α-anomer) on silica gel thin layer plates in the system methylene chloride:methanol (15:1) and optical rotation $[\alpha]_D^{20} = -39° \pm 1$ (c = 0.991 in chloroform).

EXAMPLE 2

20.0 g of ethyl-3,5,6-tri-O-benzyl-D-glucofuranoside and 12.8 g of triethylamine are dissolved in 100 ml of methylene chloride and 9.65 g of nicotinoyl chloride-hydrochloride are added in portions in the course of one hour, at about 25°, whilst stirring and with the exclusion of moisture. After the reaction mixture has been allowed to react for a further 30 minutes it is filtered. The filtrate is freed from the bulk of the methylene chloride under a waterpump vacuum and the resulting residue is dissolved in ether. The ether solution is washed with water, a saturated solution of sodium bicarbonate and again with water. The residue obtained after drying over sodium sulphate and evaporating the ether is, after degassing under a high vacuum, pure ethyl-2-O-nicotinoyl-3,5,6-tri-O-benzyl-D-glucofuranoside, which is a brownish oil with a Rf value of 0.40 on silica gel thin layer plates; system: methylene chloride/ethyl acetate (85:15), and an optical rotation $[\alpha]_D^{20} = -3.6° \pm 1°$ (c = 0.75 in chloroform).

EXAMPLE 3

In the manner described in Example 2, a solution of 25.0 g of ethyl-3-O-n-propyl-5,6-di-O-p-chlorobenzyl-D-glucofuranoside and 8 ml of pyridine in 240 ml of methylene chloride is treated with 16.0 g of nicotinoyl chloride-hydrochloride and the reaction mixture is worked up. The residue which has thus formed and has been degassed under a high vacuum is pure ethyl-2-O-nicotinoyl-3-O-n-propyl-5,6-di-O-(p-chlorobenzyl)-D-glucofuranoside, which is a brownish oil with a Rf value of 0.39 on silica gel thin layer plates in the system methylene chloride/ethyl acetate (85:15) and an optical rotation $[\alpha]_D^{20} = +39.4° \pm 0.8°$ (c = 1.092 in chloroform).

EXAMPLE 4

20 g of ethyl-3,5,6-tri-O-benzyl-D-glucofuranoside and 10 g of triethylamine are dissolved in 100 ml of methylene chloride and a solution of 13.0 g of freshly distilled isonicotinoyl chloride in 50 ml of methylene chloride is added dropwise. The reaction mixture is now treated as described in Example 2 and pure ethyl-2-O-isonicotinoyl-3,5,6-tri-O-benzyl-D-glucofuranoside is thus obtained as a brownish oil which has a Rf value of 0.56 on silica gel thin layer plates in the system methylene chloride/ethyl acetate (85:15) and an optical rotation $[\alpha]_D^{20} = -2.0° \pm 0.3°$ (c = 0.976 in chloroform).

EXAMPLE 5

In the manner described in Example 2, 20.0 g of ethyl-3,5,6-tri-O-benzyl-D-glucofuranoside and 14.0 g of triethylamine dissolved in 100 ml of methylene chloride are treated with 13.0 g of picolinoyl chloride and the reaction mixture is worked up. The residue is dissolved in 2,000 ml of methylene chloride and filtered through 400 g of silica gel (0.02–0.6 mm). After evaporating the methylene chloride solution and degassing the residue under a high vacuum, pure ethyl-2-O-(2-pyridylcarbonyl)-3,5,6-tri-O-benzyl-D-glucofuranoside is obtained as a brownish oil which has Rf values of 0.42 on silica gel thin layer plates in the system methylene chloride/ethyl acetate (85:15) and an optical rotation $[\alpha]_D^{20} = 0° \pm 1°$ (c = 1.023 in chloroform).

EXAMPLE 6

23.8 g of nicotinoyl chloride-hydrochloride are added in portions in the course of 15 minutes to a suspension of 5.0 g of 1,4-anhydro-D-glucitol (Arlitan) in 30 g of triethylamine and 100 ml of methylene chloride, at 40°, whilst stirring and with the exclusion of atmospheric moisture. After the reaction mixture has been allowed to react for a further 30 minutes, it is filtered and the bulk of the methylene chloride is distilled off from the filtrate. The residue which is thus formed from the filtrate is dissolved in methylene chloride and the solution is washed with water. After drying over sodium sulphate, evaporating under a waterpump vacuum and degassing the residue under a high vacuum, pure 2,3,5,6-tetra-O-nicotinoyl-1,4-anhydro-D-glucitol is obtained as a viscous, brownish oil which has an optical rotation $[\alpha]_D^{20} = +16° \pm 1°$ (c = 1.099 in chloroform), IR: carbonyl band at 1,730 cm$^{-1}$, and a Rf value of 0.26 on silica gel thin layer plates in the system: methylene chloride/ethyl acetate (85:15).

EXAMPLE 7

17.0 g of ethyl-3-O-methyl-5,6-di-O-benzyl-D-glucofuranoside, 11.5 g of nicotinoyl chloride-hydrochloride, 15.2 g of triethylamine and 100 ml of methylene chloride are treated, and worked up, in the manner described in Example 2. After the resulting residue has been purified by column chromatography over 1,100 g of 0.05–0.2 mm silica gel, using methylene chloride/ethyl acetate (85:15) as the running agent, pure ethyl-2-O-nicotinoyl-3-O-methyl-5,6-di-O-benzyl-D-glucofuranoside is obtained as a yellowish oil which has a Rf value of 0.32 on silica gel thin layer plates in the system: methylene chloride/ethyl acetate (85:15) and an optical rotation $[\alpha]_D^{20} = +23° \pm 1°$ (c = 1.101 in chloroform).

EXAMPLE 8

In the manner described in Example 6, pure ethyl-2-O-methyl-3,5,6-tri-O-nicotinoyl-D-glucofuranoside is obtained, as a brownish oil which has a Rf value of 0.42 ($\beta$-anomer) and 0.49 ($\alpha$-anomer) on silica gel thin layer plates; system: methylene chloride/methanol (15:1); IR: carbonyl band at 1,725 cm$^{-1}$, from 11.0 g of ethyl-2-O-methyl-D-glucofuranoside, 38.5 g of triethylamine, 130 ml of methylene chloride and 31.25 g of nicotinoyl chloride-hydrochloride.

EXAMPLE 9

In the manner described in Example 2, 20.8 g of ethyl-D-glucofuranoside, 92.5 g of nicotinoyl chloride hydrochloride, 200 ml of pyridine and 100 ml of methylene chloride are reacted, the nicotinoyl chloride-hydrochloride being added in the course of 7 hours, and the reaction mixture is worked up. The residue, which was obtained after evaporating and was degassed under a high vacuum, is pure ethyl-2,3,5,6-tetra-O-nicotinoyl-D-glucofuranoside, which is a brownish, viscous oil with a Rf value of 0.30 on silica gel thin layer plates in the system methylene chloride/methanol (15:1) and an optical rotation $[\alpha]_D^{20} = +1° \pm 1°$ (c = 0.957 in chloroform).

EXAMPLE 10

In the manner described in Example 2, a solution of 20.0 g of monoacetone-glucose in 280 ml of pyridine and 140 ml of methylene chloride is treated with 73.2 g of nicotinoyl chloride-hydrochloride and the reaction mixture is worked up. After crystallising from ether and drying under a high vacuum, this gives pure 1,2-O-isopropylidene-3,5,6-tri-O-nicotinoyl-$\alpha$-D-glucofuranose which has an optical rotation $[\alpha]_D^{20} = -86° \pm 1°$ (c = 1.028 in chloroform) and a melting point of 84°–85° and from which, in the manner described in Example 1, ethyl-3,5,6-tri-O-nicotinoyl-D-glucofuranoside is obtained with a 1 N solution of hydrogen chloride in absolute ethanol.

EXAMPLE 11

24.6 g of monoacetone-glucose are dissolved in 340 ml of pyridine and 170 ml of methylene chloride and, in the manner described in Example 2, the solution is treated with 85.0 g of isonicotinoyl chloride-hydrochloride and the reaction mixture is worked up. The residue obtained after drying over sodium sulphate, filtering and evaporating is, after degassing at 30° under a high vacuum, pure 1,2-O-isopropylidene-3,5,6-tri-O-isonicotinyl-$\alpha$-glucofuranose - Rf value 0.47 on silica gel thin layer plates in the system: chloroform/methanol (15:1), optical rotation $[\alpha]_D^{20} = -65° \pm 1°$ (c = 0.057 in chloroform) -from which, in the manner described in Example 1, ethyl-3,5,6-tri-O-isonicotinoyl-D-glucofuranoside is obtained with a 1 N solution of hydrogen chloride in absolute ethanol.

EXAMPLE 12

A solution of 25.0 g of 1,2-O-isopropylidene-3-O-n-propyl-α-D-glucofuranose in 200 ml of pyridine and 100 ml of methylene chloride is treated with 51.0 g of isonicotinoyl chloride-hydrochloride in the manner described in Example 2. The methylene chloride is then distilled off under a waterpump vacuum. 300 ml of water are added to the residue and the resulting solid product is filtered off; when crystallised from ethanol and after drying under a high vacuum this is pure 1,2-O-isopropylidene-3-O-n-propyl-5,6-di-O-isonicotinoyl-α-D-glucofuranose which has a melting point of 152°–153° and an optical rotation $[\alpha]_D^{20} = -24° \pm 1°$ (c = 0.940 in chloroform) and from which, in the manner described in Example 1, ethyl-3-O-n-propyl-5,6-di-O-isonicotinoyl-D-glucofuranoside is obtained with a 1 N solution of hydrogen chloride in absolute ethanol.

EXAMPLE 13

An ointment containing 1 percent by weight of the active compound can be manufactured in the following composition in the customary manner:

| Composition (in % by weight) | |
|---|---|
| Ethyl-2-0-methyl-3,5,6-tri-0-nicotinoyl-D-glucofuranoside | 1% |
| Anhydrous wool fat | 5% |
| Liquid paraffin | 15% |
| White petroleum jelly | 79% |

EXAMPLE 14

A solution containing 0.5 percent by weight of the active compound can be prepared in the following composition in the customary manner by dissolving the active compound in propylene glycol:

| Composition | |
|---|---|
| Ethyl-2-0-methyl-3,5,6-tri-0-nicotinoyl-D-glucofuranoside | 0.5% by weight |
| Propylene glycol | 99.5% by weight |

EXAMPLE 15

A cream containing 1 percent by weight of the active compound can be manufactured in the following composition in the customary manner:

| Composition | |
|---|---|
| Ethyl-2-0-methyl-3,5,6-tri-0-nicotinoyl-D-glucofuranoside | 1.0 g |
| Sorbitane monostearate | 1.0 g |
| Polyoxyethylene sorbitane monostearate | 4.0 g |
| Cetyl alcohol | 5.0 g |
| Stearic acid | 3.0 g |
| Liquid paraffin | 16.0 g |
| 70% sorbitol | 6.0 g |
| Methyl p-hydroxybenzoate | 0.2 g |
| Deionised water to make up to | 100.0 g |

Preparation

The fatty constituents are melted together and the active compound is mixed in. The preservative is dissolved in water and the sorbitol is added and the two mixtures are mixed whilst stirring well.

What is claimed is:

1. A furanose-O-pyridylcarboxylic acid ester of the formula I

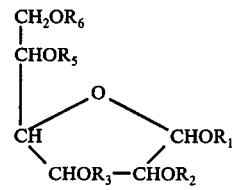

in which at least one of $R_1$, $R_2$, $R_3$, $R_5$ and $R_6$ is pyridylcarbonyl and the remainder of $R_1$, $R_2$, $R_3$, $R_5$ and $R_6$ are lower alkyl, lower alkenyl, phenyl-lower alkyl, halogenophenyl-lower alkyl, trifluoromethylphenyl-lower alkyl, lower alkylphenyl-lower alkyl, lower alkoxyphenyl-lower alkyl or hydrogen, or in which $OR_1$ is hydrogen.

2. A compound as claimed in claim 1 of the formula I, in which 1–4 of $R_1$, $R_2$, $R_3$, $R_5$ and $R_6$ are pyridylcarbonyl and the remainder of $R_1$, $R_2$, $R_3$, $R_5$ and $R_6$ are lower alkyl, lower alkenyl, phenl-lower alkyl, halogenophenyl-lower alkyl, trifluoromethylphenyl-lower alkyl, lower alkylphenyl-lower alkyl, lower alkoxyphenyl-lower alkyl or hydrogen, or in which $OR_1$ is hydrogen.

3. A compound as claimed in claim 1 of the formula I, in which 1–4 of $R_1$, $R_2$, $R_3$, $R_5$ and $R_6$ are pyridylcarbonyl and the remainder of $R_1$, $R_2$, $R_3$, $R_5$ and $R_6$ are lower alkyl, lower alkenyl, benzyl, halogenobenzyl, trifluoromethylbenzyl, lower alkylbenzyl, lower alkoxybenzyl or hydrogen, or $OR_1$ is hydrogen.

4. A compound as claimed in claim 1 of the formula I, in which 1–4 of $R_1$, $R_2$, $R_3$, $R_5$ and $R_6$ are pyridylcarbonyl and the remainder of $R_1$, $R_2$, $R_3$, $R_5$ and $R_6$ are lower alkyl with 1–3 C atoms, benzyl, chlorobenzyl or hydrogen, or $OR_1$ is hydrogen.

5. A compound as claimed in claim 1 of the formula I, in which 1–4 of $R_2$, $R_3$, $R_5$ and $R_6$ are pyridylcarbonyl and the remainder of $R_2$, $R_3$, $R_5$ and $R_6$ are lower alkyl with 1–3 C atoms, benzyl, chlorobenzyl or hydrogen and $R_1$ is lower alkyl with 1–3 C atoms.

6. A compound as claimed in claim 1 of the formula II

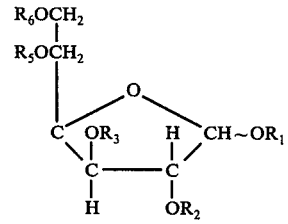

wherein $R_1$ is ethyl, $R_3$, $R_5$ and $R_6$ each represent 3-pyridylcarbonyl and $R_2$ is hydrogen, methyl or 3-pyridylcarbonyl.

7. A compound as claimed in claim 6 of the formula II wherein $R_1$ is ethyl, $R_3$, $R_5$ and $R_6$ each represent benzyl and $R_2$ is 2-, 3- or 4-pyridylcarbonyl.

8. A compound as claimed in claim 6 of the formula II, wherein $R_1$ is ethyl, $R_2$ is hydrogen, $R_3$ is 4-pyridylcarbonyl or n-propyl and $R_5$ and $R_6$ represent 4-pyridylcarbonyl.

9. A compound as claimed in claim 6 of the formula II, wherein $R_1$ is ethyl, $R_2$ is 3-pyridylcarbonyl, $R_3$ is lower alkyl and $R_5$ and $R_6$ are benzyl or p-chlorobenzyl.

10. A pharmaceutical composition comprising a therapeutically effective amount of a compound of claim 1 together with a pharmaceutically usable excipient.

* * * * *